United States Patent
Isomura

(10) Patent No.: US 9,535,015 B2
(45) Date of Patent: Jan. 3, 2017

(54) PATTERN INSPECTION METHOD AND PATTERN INSPECTION APPARATUS

(71) Applicant: NUFLARE TECHNOLOGY, INC., Yokohama, Kanagawa (JP)

(72) Inventor: Ikunao Isomura, Kanagawa (JP)

(73) Assignee: NUFLARE TECHNOLOGY, INC, Kanagawa (JP)

( * ) Notice: Subject to any disclaimer, the term of this patent is extended or adjusted under 35 U.S.C. 154(b) by 120 days.

(21) Appl. No.: 14/185,588

(22) Filed: Feb. 20, 2014

(65) Prior Publication Data

US 2014/0241611 A1    Aug. 28, 2014

(30) Foreign Application Priority Data

Feb. 25, 2013  (JP) ................ 2013-034498

(51) Int. Cl.
| | | |
|---|---|---|
| G06K 9/00 | (2006.01) | |
| G01R 31/26 | (2014.01) | |
| G01N 21/956 | (2006.01) | |
| G06T 7/00 | (2006.01) | |

(52) U.S. Cl.
CPC ............ *G01N 21/956* (2013.01); *G06T 7/001* (2013.01); *G06T 7/0008* (2013.01); *G06T 2207/30148* (2013.01)

(58) Field of Classification Search
None
See application file for complete search history.

(56) References Cited

U.S. PATENT DOCUMENTS

| | | | | |
|---|---|---|---|---|
| 8,170,072 B2 * | 5/2012 | Kawaguchi | ........ | B23K 26/0608 |
| | | | | 372/101 |
| 2002/0109090 A1 * | 8/2002 | Nakasuji | ................ | B82Y 10/00 |
| | | | | 250/311 |

(Continued)

FOREIGN PATENT DOCUMENTS

| JP | 2004349465 A | 12/2004 |
|---|---|---|
| JP | 2005516196 A | 6/2005 |

(Continued)

OTHER PUBLICATIONS

JP Office Action dated Oct. 17, 2016 for Application No. 2013034498.

*Primary Examiner* — Randolph I Chu
(74) *Attorney, Agent, or Firm* — Patterson & Sheridan LLP

(57) ABSTRACT

A pattern inspection method includes acquiring an image of a pattern in a stripe region concerned, regarding each of stripe regions of the first group each not including an adjacent stripe region in plural stripe regions obtained by virtually dividing an inspection region of a target object on which patterns have been formed into the plural stripe regions each partially overlapping an adjacent stripe region, wherein the acquiring is performed using laser lights or electron beams, in a longitudinal direction of the stripe region of the first group, and acquiring an image of a pattern in a stripe region concerned, regarding each of stripe regions of the second group each not including an adjacent stripe region, in remaining stripe regions other than the first group stripe regions, wherein the acquiring is performed using laser lights or electron beams, in the longitudinal direction of the stripe region of the second group.

13 Claims, 11 Drawing Sheets

(56) References Cited

U.S. PATENT DOCUMENTS

| | | | |
|---|---|---|---|
| 2002/0148975 A1* | 10/2002 | Kimba | G01N 23/225 250/492.1 |
| 2003/0139838 A1 | 7/2003 | Marella | |
| 2004/0032581 A1 | 2/2004 | Nikoonahad et al. | |
| 2004/0129879 A1* | 7/2004 | Furiki | H01J 37/261 250/310 |
| 2005/0045821 A1* | 3/2005 | Noji | G01N 23/225 250/311 |
| 2005/0051724 A1 | 3/2005 | Nakasuji et al. | |
| 2006/0102838 A1 | 5/2006 | Nakasuji et al. | |
| 2006/0201423 A1* | 9/2006 | Akimoto | G03F 7/162 118/712 |
| 2007/0156379 A1 | 7/2007 | Kulkarni et al. | |
| 2007/0230770 A1 | 10/2007 | Kulkarni et al. | |
| 2007/0288219 A1 | 12/2007 | Zafar et al. | |
| 2009/0206257 A1 | 8/2009 | Gunji et al. | |
| 2009/0297019 A1 | 12/2009 | Zafar et al. | |
| 2010/0119144 A1 | 5/2010 | Kulkarni et al. | |
| 2011/0286656 A1 | 11/2011 | Kulkarni et al. | |
| 2014/0231813 A1* | 8/2014 | Oda | H01L 21/02532 257/66 |
| 2015/0154746 A1 | 6/2015 | Zafar et al. | |
| 2015/0204796 A1* | 7/2015 | Nagahama | G01N 21/8806 356/237.5 |

FOREIGN PATENT DOCUMENTS

| | | |
|---|---|---|
| JP | 2009516832 A | 4/2009 |
| JP | 2009117541 A | 5/2009 |
| JP | 2009192345 | 8/2009 |

* cited by examiner

PATTERN INSPECTION METHOD AND PATTERN INSPECTION APPARATUS

CROSS-REFERENCE TO RELATED APPLICATION

This application is based upon and claims the benefit of priority from the prior Japanese Patent Application No. 2013-034498 filed on Feb. 25, 2013 in Japan, the entire contents of which are incorporated herein by reference.

BACKGROUND OF THE INVENTION

Field of the Invention

The present invention generally relates to a pattern inspection apparatus and a pattern inspection method. More specifically, for example, it relates to an inspection apparatus that inspects a pattern by irradiating laser lights or electron beams so as to acquire an optical image of the pattern to be inspected, and to a method therefor.

Description of Related Art

In recent years, with the advance of high integration and large capacity of a large scale integrated circuit (LSI), the line width (critical dimension) required for circuits of semiconductor elements is becoming progressively narrower. Such semiconductor elements are manufactured by exposing and transferring a pattern onto a wafer to form a circuit by means of a reduced projection exposure apparatus, which is known as a stepper, by using an original or "master" pattern (also called a mask or a reticle, and will be generically referred to as a mask hereinafter) with a circuit pattern formed thereon. Then, in manufacturing the mask used for transferring such a fine circuit pattern onto a wafer, a pattern writing apparatus capable of writing or "drawing" fine circuit patterns by using electron beams needs to be employed. Pattern circuits may be written directly on the wafer by the pattern writing apparatus. Also, a laser beam writing apparatus that uses laser beams in place of electron beams for writing a pattern is under development.

Since LSI manufacturing requires a tremendous amount of manufacturing cost, it is crucial to improve its yield. However, as typified by a 1-gigabit DRAM (Dynamic Random Access Memory), the scale of a pattern configuring an LSI has been changing from on the order of submicron to nanometer. One of major factors that decrease the yield of the LSI manufacturing is a pattern defect of a mask used when exposing and transferring a fine pattern onto a semiconductor wafer by the photolithography technology. In recent years, with miniaturization of an LSI pattern formed on a semiconductor wafer, dimensions to be detected as a pattern defect have become extremely small. Thus, a pattern inspection apparatus for inspecting a defect of a transfer mask used in manufacturing LSI needs to be highly accurate.

Meanwhile, with development of multimedia technology, the size of LCD (Liquid Crystal Display) substrate is becoming larger, e.g., 500 mm×600 mm or greater, and the size of a pattern such as a TFT (Thin Film Transistor) or the like formed on the liquid crystal substrate is becoming finer. Therefore, it is increasingly required that an extremely small defect of a pattern should be inspected in a large range. For this reason, development of a pattern inspection apparatus that can efficiently and short-timely inspect a defect of a photomask used when manufacturing large area LCD patterns and large-area LCDs is urgently required.

As an inspection method, there is known a method of comparing an optical image of a pattern, formed on a target object or "sample", such as a lithography mask, imaged at a predetermined magnification by using a magnifying optical system with design data or an optical image obtained by imaging the same pattern on the target object. For example, the following is known as pattern inspection methods: die-to-die inspection method that compares data of optical images of identical patterns at different positions on the same mask; and die-to-database inspection method that inputs, into the inspection apparatus, writing data (design pattern data) which is generated by converting pattern-designed CAD data to a writing apparatus specific format for input when writing a pattern on the mask, generates design image data (reference image) based on the input writing data, and compares the generated design image data with an optical image (serving as measurement data) obtained by imaging the pattern. According to the inspection method for use in such an inspection apparatus, a target object is placed on the stage so that a light flux may scan the object by the movement of the stage in order to perform an inspection. Specifically, the target object is irradiated with a light flux from the light source and the illumination optical system. Light transmitted through the target object or reflected therefrom is focused on a sensor through the optical system. An image captured by the sensor is transmitted as measurement data to the comparison circuit. In the comparison circuit, after performing position alignment of images, measurement data and reference data are compared with each other in accordance with an appropriate algorithm. If there is no matching between the compared data, it is determined that a pattern defect is present.

When performing the pattern inspection, the existence or nonexistence of a defect of a pattern in a stripe region is inspected by dividing the whole of an inspection region of a target object into a plurality of strip-shaped stripe regions and scanning a stripe region concerned in the longitudinal direction with inspection beams. In that case, inspection is performed in order for a next stripe region adjacent to the stripe region having been inspected. With the current trend of miniaturization of patterns, it is necessary to strengthen (increase) the light intensity of a deep ultraviolet (DUV) light used as an inspection light. For this reason, the stripe region having been inspected is heated by the scanning using by a laser light. Thus, if the same stripe region is inspected twice, characteristics of an image acquired for the first time and characteristics of an image acquired for the second time after the heating are completely different from each other. Such heat affects not only the stripe region concerned but also the adjacent stripe region. Usually, adjacent stripe regions are set to be mutually slightly overlapping so as to avoid omission of detection of a defect at the boundary. Therefore, when scanning a stripe region concerned to be inspected, a part of the adjacent stripe region is also scanned. Thus, there is a problem that, because of the influence of the heat, it becomes difficult to acquire a highly precise image even in inspecting an adjacent stripe region.

As pattern miniaturization further advances, since resolution limit may be exceeded when using a DUV light source. Therefore, an inspection apparatus that uses electron beams whose resolution is higher than that of a DUV light source will be needed. However, if a stripe region is scanned in the longitudinal direction with an electron beam, electron charge-up occurs in the stripe region having been inspected. Then, when the same stripe region is inspected twice, an image acquired for the first time and an image acquired for the second time after the charging up are completely different from each other. Such charge-up affects not only the stripe region concerned but also the adjacent stripe region.

As described above, adjacent stripe regions are set to be mutually slightly overlapping so as to avoid omission of detection of a defect at the boundary. Therefore, when scanning a stripe region concerned to be inspected, a part of the adjacent stripe region is also scanned. Thus, there is a problem that, because of the influence of the charging up, it becomes difficult to acquire a highly precise image even in inspecting an adjacent stripe region.

As technique related to the inspection apparatus that performs inspection using electron beams, there is disclosed an inspection apparatus in which an image of one line in a stripe region concerned is obtained by performing scanning in a single stroke of an electron beam in the short side direction of the stripe region to be inspected (refer to, e.g., Japanese Patent Application Laid-open (JP-A) No. 2009-192345). The technique employed in this inspection apparatus is to repeat a line scanning back and forth for going scanning and returning scanning of the same line in order to perform image acquisition and perform discharging, etc. of the region having just been charged.

As mentioned above, there is a problem that the image of an adjacent stripe region is distorted by inspecting (scanning) a target stripe region. However, a method sufficient for solving this problem has not been established yet.

BRIEF SUMMARY OF THE INVENTION

In accordance with one aspect of the present invention, a pattern inspection method includes acquiring an image of a figure pattern arranged in a stripe region concerned, with respect to each of stripe regions of a first group each not including an adjacent stripe region in a plurality of stripe regions obtained by virtually dividing an inspection region of a target object on which a plurality of figure patterns have been formed into the plurality of stripe regions each having a strip shape and overlapping a part of an adjacent stripe region, wherein the acquiring is performed using one of a laser light and an electron beam, in a longitudinal direction of the stripe region concerned of the first group; and acquiring, after the acquiring the image of the figure pattern has been completed for all of the stripe regions of the first group, an image of a figure pattern arranged in a stripe region concerned, with respect to each of stripe regions of a second group each not including an adjacent stripe region, in remaining stripe regions other than the stripe regions of the first group in the plurality of stripe regions, wherein the acquiring is performed using one of the laser light and the electron beam, in the longitudinal direction of the stripe region concerned of the second group.

In accordance with another aspect of the present invention, a pattern inspection method includes inspecting a defect of a figure pattern arranged in a stripe region concerned, with respect to each of stripe regions of a first group each not including an adjacent stripe region in a plurality of stripe regions obtained by virtually dividing an inspection region of a target object on which a plurality of figure patterns are formed into the plurality of stripe regions each having a strip shape and overlapping a part of an adjacent stripe region, wherein the inspecting is performed using one of a laser light and an electron beam, in a longitudinal direction of the stripe region concerned of the first group; cooling the target object after the inspecting the defect of the figure pattern has been completed for all of the stripe regions of the first group; and inspecting, after the cooling, a defect of a figure pattern arranged in a stripe region concerned, with respect to each of stripe regions of a second group each not including an adjacent stripe region, in remaining stripe regions other than the stripe regions of the first group in the plurality of stripe regions, wherein the inspecting is performed using one of the laser light and the electron beam, in the longitudinal direction of the stripe region concerned of the second group.

Moreover, in accordance with another aspect of the present invention, a pattern inspection apparatus includes an inspection chamber where inspection of a defect of a figure pattern of a target object on which a plurality of figure patterns are formed is performed using one of a laser light and an electron beam; and a cooling unit arranged outside the inspection chamber and configured to cool the target object.

Furthermore, in accordance with another aspect of the present invention, a pattern inspection apparatus includes an inspection chamber where inspection of a defect of a figure pattern of a target object on which a plurality of figure patterns are formed is performed using one of a laser light and an electron beam; and an electric discharge unit arranged outside the inspection chamber and configured to discharge from the target object.

DETAILED DESCRIPTION OF THE INVENTION

In the following embodiments, there will be described an inspection apparatus and method that can eliminate the influence of an adjacent stripe region when acquiring an image per stripe region by scanning with a laser beam or an electron beam.

First Embodiment

Figure 1:
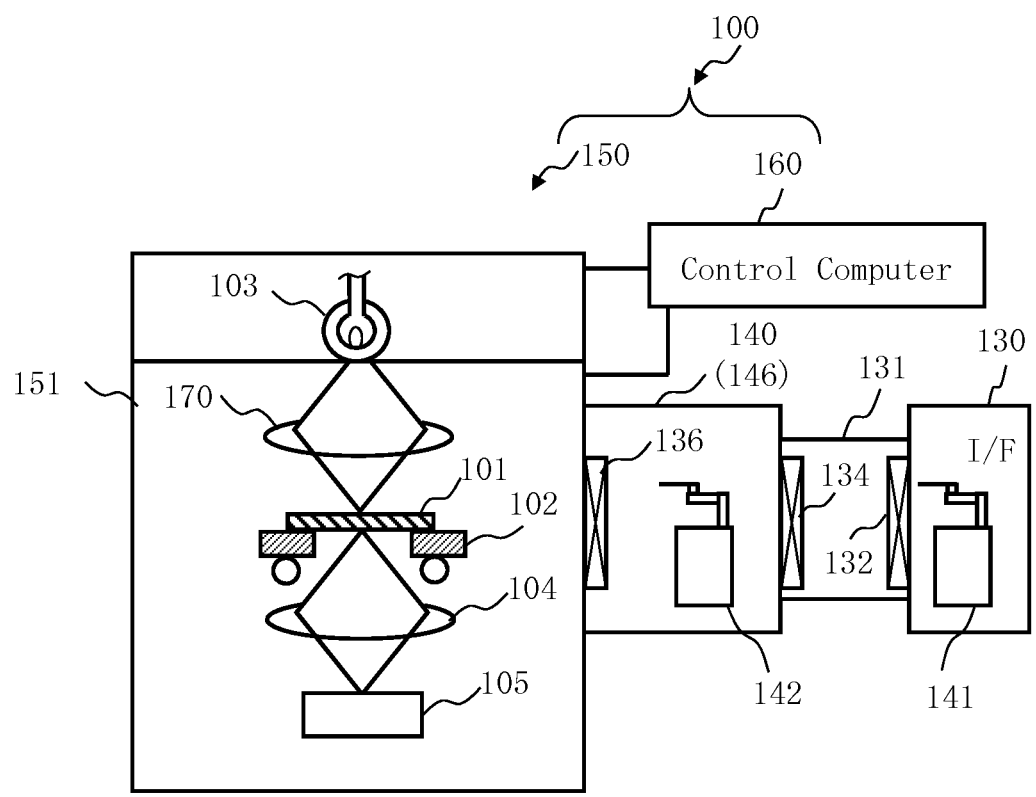
FIG. 1 is a schematic diagram showing a structure of a pattern inspection apparatus according to the first embodiment.

FIG. 1 is a schematic diagram showing a structure of a pattern inspection apparatus according to the first embodiment. In FIG. 1, an inspection apparatus 100 that inspects a defect of a pattern formed on a target object, such as a mask, includes an inspection unit 150, a control system circuit 160 (control unit), an input/output interface (I/F) 130, a load lock chamber 131, a robot chamber 140, and a cooling chamber 146. The inspection unit 150 includes a light source 103 and an inspection chamber 151.

In the inspection chamber 151, there are arranged an illumination optical system 170, an XYθ table 102 arranged movably, a magnifying optical system 104, and a photo-diode array 105 (an example of a sensor). On the XYθ table 102, a target object 101 is placed. In the input/output interface 130, a transfer robot 141 for transferring the target object 101 is arranged. In the robot chamber 140, a transfer robot 142 for transferring the target object 101 is arranged. At the boundaries each between two of the input/output interface 130, the load lock chamber 131, the robot chamber 140, and the inspection chamber 151, there are arranged gate valves 132, 134, and 136. The target object 101 is, for example, an exposure mask substrate used for transferring a pattern onto the wafer. A pattern composed of a plurality of figures to be inspected is formed on this mask substrate.

FIG. 1 shows a configuration necessary for describing the first embodiment. It should be understood that other configuration elements generally necessary for the inspection apparatus 100 may also be included therein. The transfer robots 141 and 142 may be any as long as they are mechanical systems, such as an elevator mechanism and a rotation mechanism.

Figure 2:
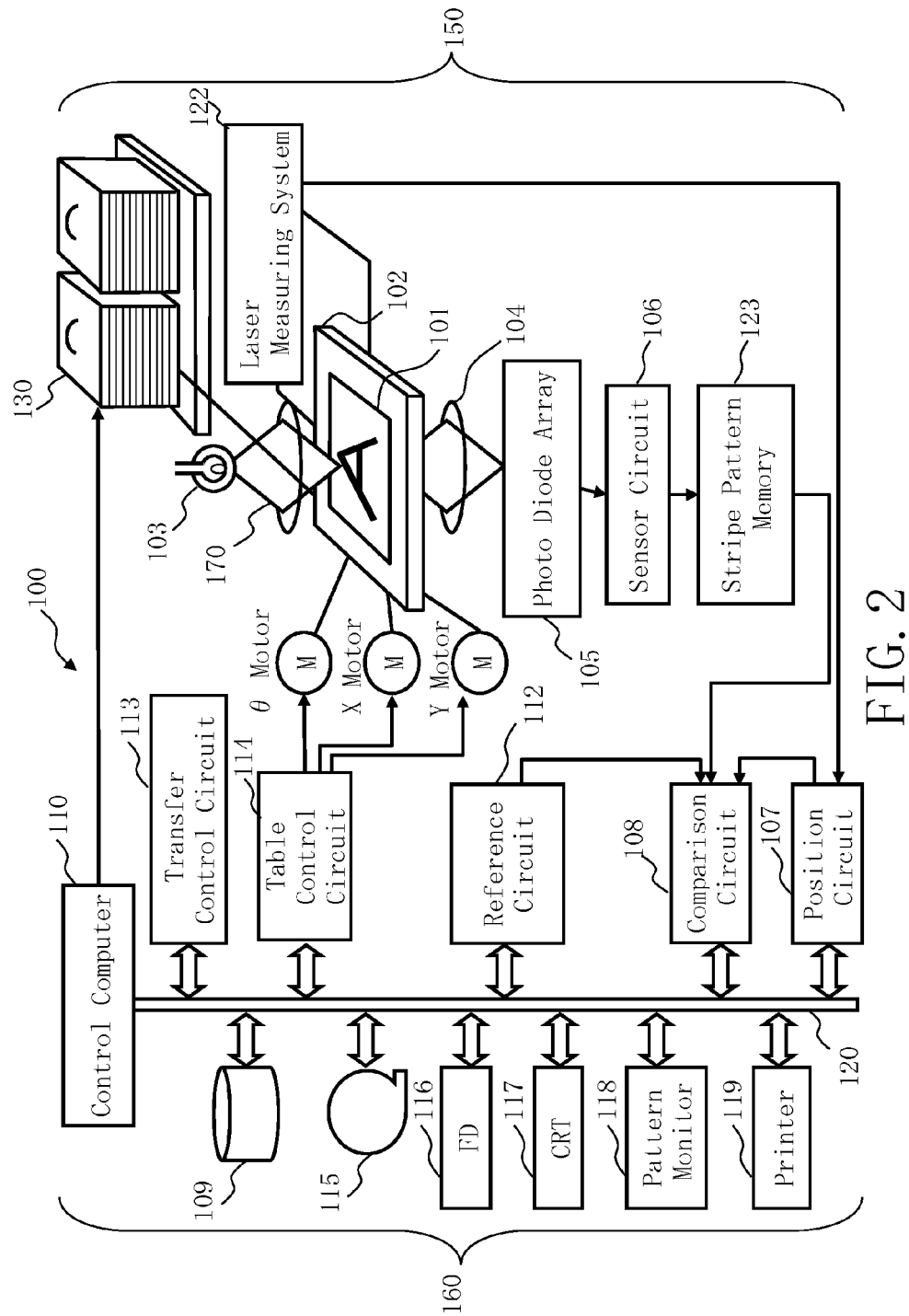
FIG. 2 is a conceptual diagram showing a configuration of an inspection apparatus according to the first embodiment.

FIG. 2 is a conceptual diagram showing a configuration of an inspection apparatus according to the first embodiment. In FIG. 2, the inspection unit 150 further includes a sensor circuit 106, a stripe pattern memory 123, and a laser measuring system 122. In the control system circuit 160, a control computer 110 is connected, through a bus 120, to a position circuit 107, a comparison circuit 108, a reference circuit 112, a transfer control circuit 113, a table control circuit 114, a magnetic disk drive 109, a magnetic tape drive 115, a flexible disk drive (FD) 116, a CRT 117, a pattern monitor 118, and a printer 119. Moreover, the sensor circuit 106 is connected to the stripe pattern memory 123 which is connected to the comparison circuit 108. The XYθ table 102 is driven by an X-axis motor, a Y-axis motor, and a θ-axis motor. The XYθ table 102 serves as an example of the stage.

In the inspection apparatus 100, an inspection optical system of large magnification is composed of the light source 103, the XYθ table 102, the illumination optical system 170, the magnifying optical system 104, the photo diode array 105, and the sensor circuit 106. The XYθ table 102 is driven by the table control circuit 114 under the control of the control computer 110. The XYθ table 102 can be moved by a drive system such as a three-axis (X, Y, and θ) motor, which drives in the directions of x, y, and θ. For example, a step motor can be used as each of these X, Y, and θ motors. The XYθ table 102 is movable in the horizontal direction and a rotation direction by the X-, Y-, and θ-axis motors. The moving position of the XYθ table 102 is measured by the laser measuring system 122 and supplied to the position circuit 107.

The photo-mask 101 serving as an inspection target object, on which a plurality of figure patterns are formed, is placed on the XYθ table 102 by the transfer operation controlled by the transfer control circuit 113 to be described later. Then, the patterns formed on the photo-mask 101 are irradiated by an inspection light (e.g., a DUV light) of a wavelength of or below the ultraviolet region emitted from the suitable light source 103 through the illumination optical system 170. Light transmitted through the photo-mask 101 is focused as an optical image on the photo diode array 105 via the magnifying optical system 104, and enters thereinto.

It is preferable to use, for example, a TDI (Time Delay Integration) sensor and the like as the photo diode array 105.

Figure 3:
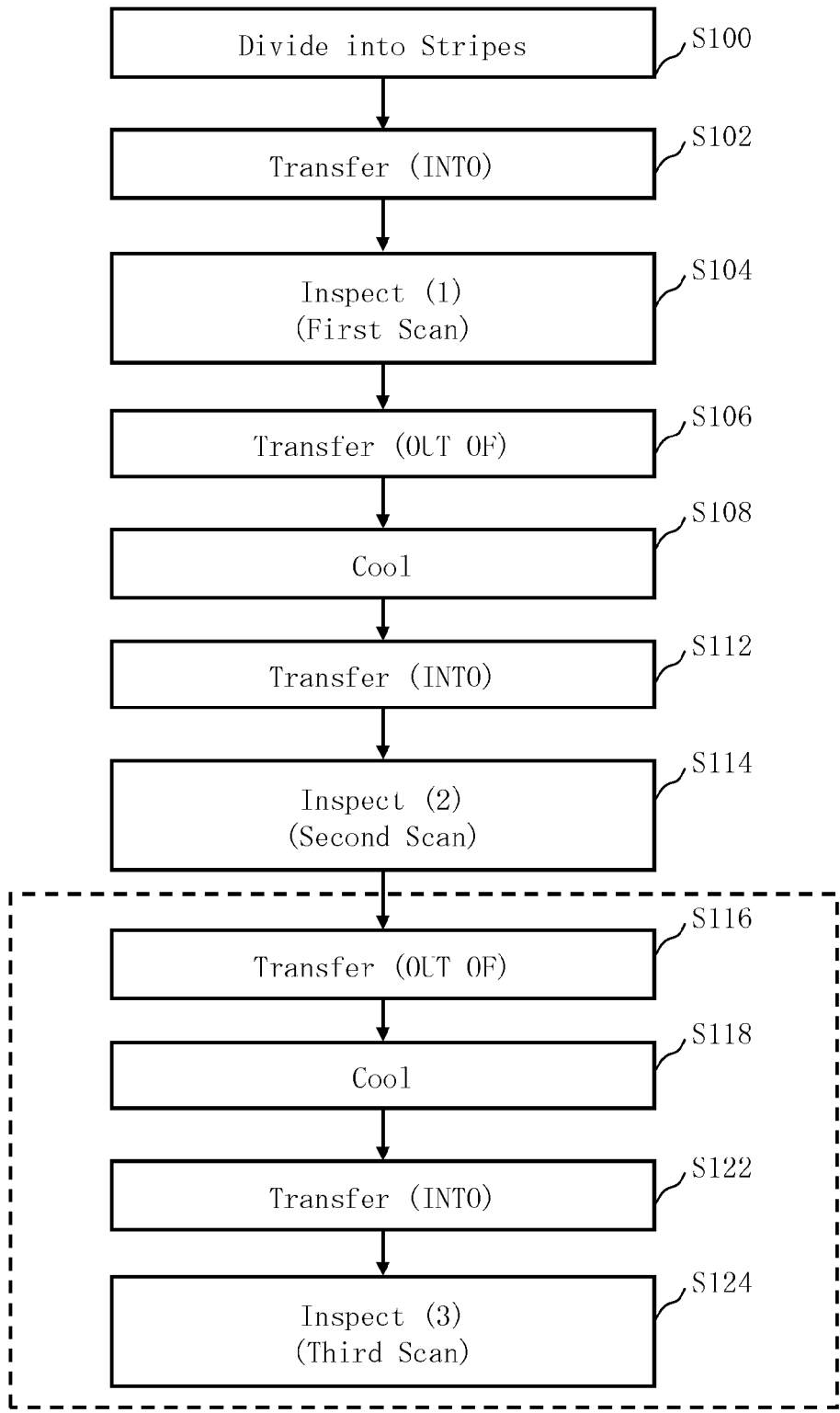
FIG. 3 is a flowchart showing main steps of an inspection method according to the first embodiment.

FIG. 3 is a flowchart showing main steps of an inspection method according to the first embodiment. In FIG. 3, the inspection method according to the first embodiment executes a series of steps: a step (S100) of dividing into stripes, a transferring-in step (S102), an inspection (1) step (S104), a transferring-out step (S106), a cooling step (S108), a transferring-in step (S112), and an inspection (2) step (S114). Here, the case of separating a plurality of inspection stripes 20 into two groups (stripe region groups) is shown. Moreover, when separating a plurality of inspection stripes 20 into three groups as to be described later, further, a series of steps of a transferring-out step (S116), a cooling step (S118), a transferring-in step (S122), and an inspection (3) step (S124) is executed.

In the step (S100) of dividing into stripes, the inspection region of a target object, where a plurality of figure patterns are formed, is divided into a plurality of strip-shaped stripe regions.

Figure 4:
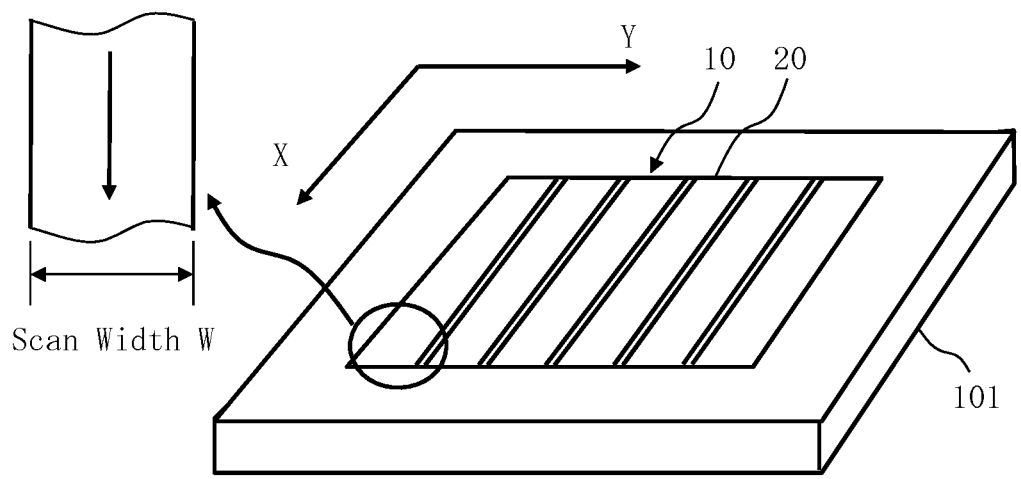
FIG. 4 is a conceptual diagram illustrating an inspection region according to the first embodiment.

FIG. 4 is a conceptual diagram illustrating an inspection region according to the first embodiment. As shown in FIG. 4, an inspection region 10 (entire inspection region) of the target object 101 is virtually divided into a plurality of strip-shaped inspection stripes 20 (an example of a small region or a stripe region) each having a scan width W in the y direction, for example. Portions of the adjacent inspection stripes 20 are set to be overlapped with each other. It is preferable for the portion overlapped to be a region for several pixels. As will be described below, an image is acquired for each inspection stripe 20 in the inspection apparatus 100, and portions of adjacent inspection stripes 20 overlap with each other in order to avoid omission of image acquisition near the boundary between the adjacent inspection stripes 20.

Figure 5:
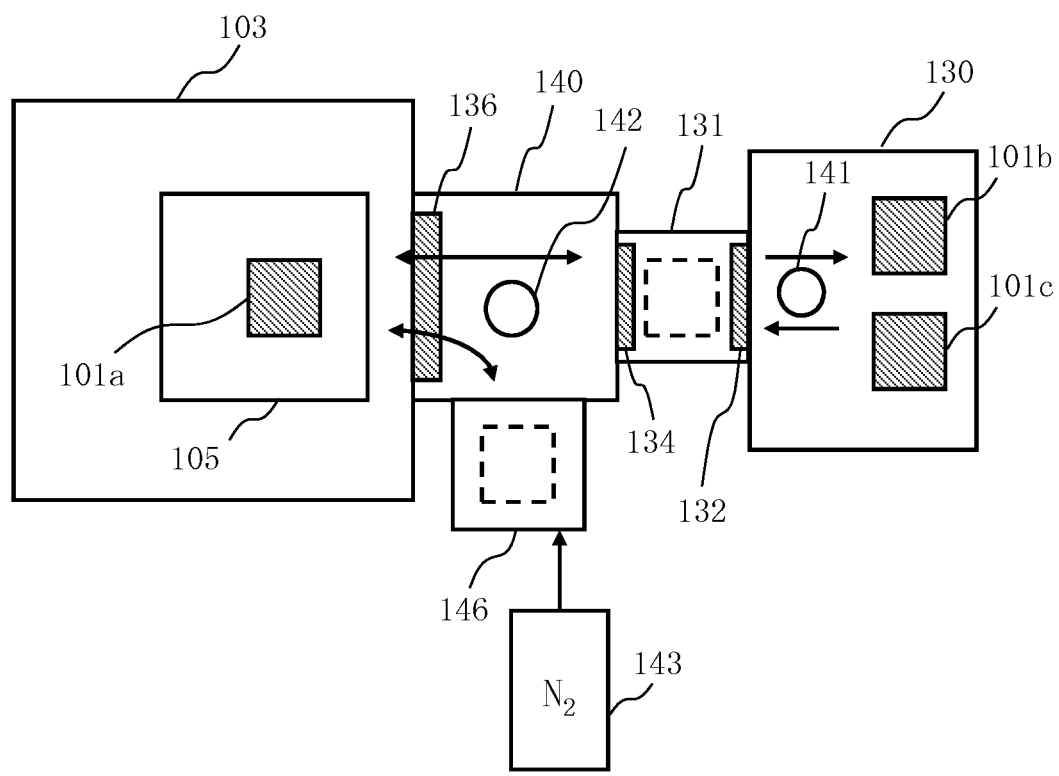
FIG. 5 is a top view schematic diagram showing a transfer route in an inspection apparatus according to the first embodiment.

In the transferring-in step (S102), the target object 101 is transferred into the inspection chamber 151. Specifically, it operates as follows:

FIG. 5 is a top view schematic diagram showing a transfer route in an inspection apparatus according to the first embodiment. After the gate valve 132 is opened, the target object 101 arranged in the input/output interface 130 (on the autoloader) is transferred to the stage in the load lock chamber 131 by the transfer robot 141. Then, after the gate valve 132 is closed, the gate valve 134 is opened in order to transfer the target object 101 onto the XYθ table 102 in the inspection chamber 151 through the robot chamber 140 by the transfer robot 142.

In the inspection (1) step (S104), after the target object 101 is placed on the XYθ table 102 and the gate valve 136 is closed, inspection of a pattern formed on the target object 101 on the XYθ table 102 is carried out. Here, inspection (the first scan) (the first image acquisition) is performed with respect to inspection stripes 20 of the first group (the first stripe region group) in a plurality of inspection stripes 20.

Figure 6:
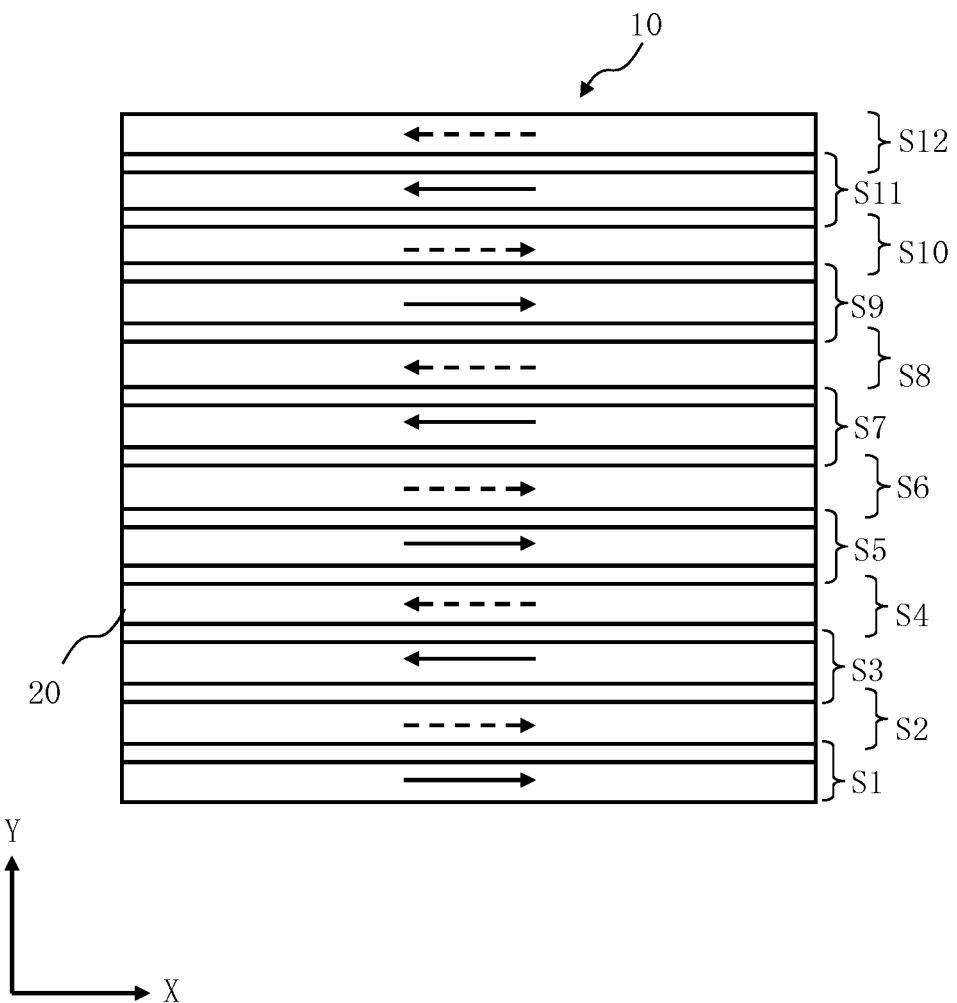
FIG. 6 shows an example of a scanning procedure according to the first embodiment.

FIG. 6 shows an example of a scanning procedure according to the first embodiment. First, inspection stripes 20 of the first group are set in a plurality of inspection stripes 20. The first group inspection stripes 20 are configured by inspection stripes S1, S3, S5, . . . , each of which does not include the adjacent stripe region. In the case of FIG. 6, a set of every other inspection stripes 20 in a plurality of inspection stripes 20 is specified as the first group inspection stripes 20. A set of the remaining every other inspection stripes 20, such as S2, S4, S6, . . . , is specified as the second group inspection stripes 20.

Then, with respect to each of the inspection stripes 20 of the first group, defect inspection is performed for a figure pattern arranged in a stripe region concerned using a laser light, in the longitudinal direction (the x direction) of the stripe region concerned. Here, the movement of the XYθ table 102 is controlled such that the inspection stripes 20 of the first group are scanned continuously. Optical images are acquired by the photo diode array 105 moving relatively in the x direction continuously by the movement of the XYθ table 102. That is, the photo diode array 105 continuously captures optical images each having a scan width W as shown in FIG. 4. In other words, the photo diode array 105, being an example of a sensor, captures optical images of a plurality of figure patterns formed on the photo-mask 101 by using an inspection light, while moving relatively to the XYθ table 102 (stage). According to the first embodiment, after capturing an optical image in one inspection stripe 20 (for example, S1), the photo diode array 105 moves in the y direction to the position of the next inspection stripe 20 (for example, S3) of the same group and similarly captures another optical image having the scan width W continuously while moving in the direction reverse to the last image capturing direction. That is, the image capturing is repeated in the forward(FWD) to backward(BWD) direction, namely going in the reverse direction when advancing and returning.

The direction of the image capturing is not limited to repeating the forward(FWD) and backward(BWD) movement. It is also acceptable to capture an image from a fixed one direction with respect to each inspection stripe 20 of the same group. For example, repeating FWD and FWD may be sufficient, and alternatively, BWD and BWD may also be sufficient.

A pattern image focused on the photo diode array 105 is photoelectrically converted by each light receiving element of the photo diode array 105, and is further analog-to-digital (A/D) converted by the sensor circuit 106. Then, pixel data for each inspection stripe is stored in the stripe pattern memory 123. The pixel data is sent to the comparison circuit 108, with data indicating the position of the photo-mask 101 on the XYθ table 102 output from the position circuit 107. Measurement data is 8-bit unsigned data, for example, and indicates a gray level (light intensity) of brightness of each pixel.

In the reference image generation step, the reference circuit 112 reads design data in order with respect to each inspection stripe 20 of the inspection target group from the magnetic disk drive 109 through the control computer 110. The read design data for the photo-mask 101 is converted into image data of binary values or multiple values in order to generate reference data (reference image). The reference data is 8-bit unsigned data, for example, and indicates a gray level (light intensity) of brightness of each pixel. The reference data is generated so that it may become an image of a predetermined size, and then, sent to the comparison circuit 108.

In the comparison step, the comparison circuit 108 (comparison unit) inputs, for each inspection stripe 20, measurement data (optical image) from the stripe pattern memory 123. The measurement data for a stripe is divided into a plurality of frame images so that it may become an image of a predetermined size. On the other hand, reference data (reference image) is input from the reference circuit 112.

Then, position alignment is performed between corresponding measurement data and reference data for an image (a frame image) of a predetermined size. Each frame image of a plurality of frame images and its corresponding reference image are compared for each pixel, in accordance with a predetermined algorithm. In other words, each pixel data of measurement data and reference pixel data of reference data are compared with each other for each pixel in accordance with a predetermined algorithm in order to determine the existence or nonexistence of a defect. For example, it is determined based on whether a pixel value difference between measurement data and reference data is within a threshold value or not. Then, the comparison result is output, for example, to the magnetic disk drive 109, magnetic tape drive 115, FD 116, CRT 117, pattern monitor 118, or printer 119. Alternatively, it may be output to the outside.

As described above, first, pattern defect inspection is performed with respect to inspection stripes 20 of the first group. Through the above inspection (1) step (S104), the inspection stripes 20 of the first group have been heated by a laser light. For example, DUV light of 200 mW is irradiated. Since the temperature of an overlapping portion increases when irradiation density is high, the temperature at an overlapping portion between each of the first group inspection stripes 20 and its adjacent inspection stripe 20 also goes up. Therefore, in this state, if scanning is performed for an inspection stripe 20 adjacent to each of the inspection stripes 20 of the first group, image characteristics acquired at the adjacent inspection stripe 20 may be changed and different from those of the inspection stripes 20 of the first group. Thus, according to the first embodiment, the target object 101 is once cooled before carrying out the inspection (2) step (S114).

In the transferring-out step (S106), when a pattern defect inspection has been completed with respect to all the inspection stripes 20 of the first group, the gate valve 136 is opened in order to move (transfer) the target object 101 from the XYθ table 102 in the inspection chamber 151 into the robot chamber 140 by the transfer robot 142. Then, after the gate valve 136 is closed, the target object 101 is transferred to the stage in the cooling chamber 146.

In the cooling step (S108), the target object 101 is cooled in the cooling chamber 146 (an example of a cooling unit). As a cooling mechanism, nitrogen ($N_2$) gas is supplied onto the surface of the target object 101 from a nitrogen ($N_2$) supply circuit 143 (an example of the cooling unit), for example. Thereby, the surface of target object 101 is cooled. In cooling, it is more preferable that the $N_2$ gas is supplied only onto the inspection stripes 20 of the first group for which scanning has been carried out. In that case, it should be understood that the overlapping portion of the adjacent inspection stripe 20 is also a supply target. The coolant gas is not limited to $N_2$ gas, and it is acceptable to use other gas as long as it does not affect a pattern. For example, it is also preferable to use noble element gases besides $N_2$ gas. The heat resulting from scanning the inspection stripes 20 of the first group can be eliminated by cooling the target object 101.

In the transferring-in step (S112), after the target object 101 has been cooled, the target object 101 is moved (transferred) into the robot chamber 140 from the stage in the cooling chamber 146 by the transfer robot 142. Then, the gate valve 136 is opened in order to transfer the target object 101 to the XYθ table 102 in the inspection chamber 151.

Although the cooling chamber 146 is intentionally provided for cooling in the example described above, it is not limited thereto. It is also preferable to perform cooling during the transfer. Alternatively, it is also preferable to release heat from the target object 101 by controlling the transfer time without positively performing a cooling operation. According to the first embodiment, although it is not excluded to perform cooling in the inspection chamber 151, it is more preferable to take the target object 101 out of the inspection chamber 151 to be certainly cooled.

In the inspection (2) step (S114), after the target object 101 is placed on the XYθ table 102 and the gate valve 136 is closed, inspection (2) of a pattern formed on the target object 101 on the XYθ table 102 is carried out. Here, inspection (the second scan) (the second image acquisition) is performed with respect to inspection stripes 20 of the second group (the second stripe region group) in a plurality of inspection stripes 20.

Then, with respect to each of the inspection stripes 20, such as S2, S4, S6, . . . , of the second group, defect inspection is performed for a figure pattern arranged in a stripe region concerned using a laser light, in the longitudinal direction (the x direction) of the stripe region concerned. Here, the movement of the XYθ table 102 is controlled such that the inspection stripes 20 of the second group are scanned continuously. The inspection method is the same as that for inspection stripes 20 of the first group. In other words, after capturing an optical image in one inspection stripe 20 (for example, S2), the photo diode array 105 moves in the y direction to the position of the next inspection stripe 20 (for example, S3) of the same group in order to similarly capture another optical image having the scan width W continuously while moving in the direction reverse to the last image capturing direction. That is, the image capturing is repeated in the forward(FWD) to backward(BWD) direction, namely going in the reverse direction when advancing and returning.

As described above, in the example of FIG. 6, each of every other inspection stripes 20 in a plurality of inspection stripes 20 obtained by dividing the entire inspection region of the target object 101 is scanned with a laser beam as the first scan. After the first scanning, cooling is performed. Then, each of the remaining every other inspection stripes 20 is scanned with a laser beam as the second scan. Thereby, the influence of the heat generated by scanning the adjacent inspection stripe 20 can be eliminated. Therefore, the influence of the heat generated by the first scan has been eliminated when performing the second image acquisition.

Figure 7:
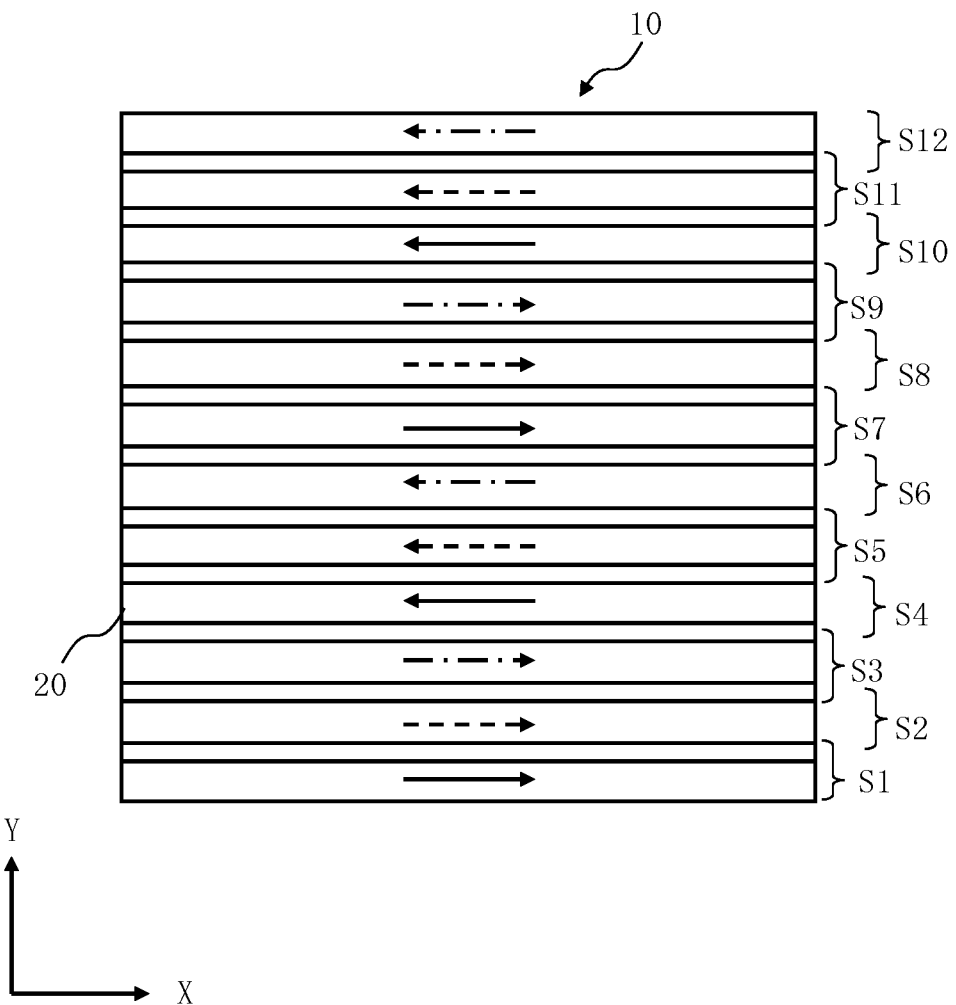
FIG. 7 shows another example of the scanning procedure according to the first embodiment.

FIG. 7 shows another example of the scanning procedure according to the first embodiment. Although every other inspection stripes 20 in a plurality of inspection stripes 20 are grouped in the example of FIG. 6, it is not limited thereto. FIG. 7 illustrates an example where every three inspection stripes 20 are grouped. First, inspection stripes 20 of the first group are set in a plurality of inspection stripes 20. The first group inspection stripes 20 are configured by inspection stripes 20, such as S1, S4, S7, . . . , which are every three inspection stripes and each of which does not include the adjacent stripe region. The second group inspection stripes 20 are configured by inspection stripes 20, such as S2, S5, S8, . . . , which are every three inspection stripes and each of which does not include the adjacent stripe region. The third group inspection stripes 20 are configured by inspection stripes 20, such as S3, S6, S9, . . . , which are every three inspection stripes and each of which does not include the adjacent stripe region.

After performing each step from the step (S100) of dividing into stripes to the inspection (2) step (S114) described above, further the transferring-out step (S116), the cooling step (S118), the transferring-in step (S122), and the inspection (3) step (S124) are carried out. The inspection (1) step (S104) is executed not for S1, S3, S5, . . . , which are every other inspection stripes 20 but for S1, S4, S7, . . . , which are every three inspection stripes 20. Similarly, the inspection (2) step (S114) is executed not for S2, S4, S6, . . . , which are every other inspection stripes 20 but for S2, S5, S8, . . . , which are every three inspection stripes 20.

In the transferring-out step (S116), when a pattern defect inspection has been completed with respect to all the inspection stripes 20 of the second group, the gate valve 136 is opened in order to move (transfer) the target object 101 from the XYθ table 102 in the inspection chamber 151 into the robot chamber 140 by the transfer robot 142. Then, after the gate valve 136 is closed, the target object 101 is transferred to the stage in the cooling chamber 146.

In the cooling step (S118), the target object 101 is cooled in the cooling chamber 146. The cooling method is the same as that of the cooling step (S108).

In the transferring-in step (S122), after the target object 101 has been cooled, the target object 101 is moved (transferred) into the robot chamber 140 from the stage in the cooling chamber 146 by the transfer robot 142. Then, the gate valve 136 is opened in order to transfer the target object 101 to the XYθ table 102 in the inspection chamber 151.

In the inspection (3) step (S124), after the target object 101 is placed on the XYθ table 102 and the gate valve 136 is closed, inspection (3) of a pattern formed on the target object 101 on the XYθ table 102 is carried out. Here, inspection (the third scan) (the third image acquisition) is performed with respect to inspection stripes 20 of the third group (the third stripe region group) in a plurality of inspection stripes 20.

Then, with respect to each of the inspection stripes 20, such as S3, S6, S9, . . . , of the third group, defect inspection is performed for a figure pattern arranged in a stripe region concerned using a laser light, in the longitudinal direction (the x direction) of the stripe region concerned. Here, the movement of the XYθ table 102 is controlled such that the inspection stripes 20 of the third group are scanned continuously. The inspection method is the same as that for the inspection stripes 20 of the second group. In other words, after capturing an optical image in one inspection stripe 20 (for example, S3), the photo diode array 105 moves in the y direction to the position of the next inspection stripe 20 (for example, S6) of the same group in order to similarly capture another optical image having the scan width W continuously while moving in the direction reverse to the last image capturing direction. That is, the image capturing is repeated in the forward(FWD) to backward(BWD) direction, namely going in the reverse direction when advancing and returning.

As described above, in the example of FIG. 7, each of every three inspection stripes 20 in a plurality of inspection stripes 20 obtained by dividing the entire inspection region of the target object 101 is scanned with a laser beam as the first scan. After the first scanning, cooling is performed. Then, each of the remaining every three inspection stripes 20 is scanned with a laser beam as the second scan. After the second scanning, cooling is performed again. Then, each of the remaining every three inspection stripes 20 is scanned with a laser beam as the third scan. Thereby, the influence of the heat generated by scanning the adjacent inspection stripe 20 can be eliminated. Therefore, the influence of the heat generated by the first scan has been eliminated when performing the second image acquisition. Furthermore, the influence of the heat generated by the second scan (and the first scan) has been eliminated when performing the third image acquisition.

Then, after the inspection of all the inspection stripes has been completed, the gate valve 136 is opened in order to transfer the target object 101 into the robot chamber 140 from the XYθ table 102 in the inspection chamber 151 by the transfer robot 142. After the gate valve 136 is closed, the gate valve 134 is opened in order to transfer the target object 101 onto the stage in the load lock chamber 131 by the transfer robot 142. Then, after the gate valve 134 is closed, the gate valve 132 is opened in order to transfer the target object 101 to the input/output interface 130 by the transfer robot 141.

As described above, according to the first embodiment, inspection stripes 20 adjacent to each other are separated into different groups in order to perform scanning per group with a laser light, and the target object is cooled between the scanning of each group. Thereby, the influence of the heat generated by scanning the adjacent inspection stripe 20 can be eliminated. Particularly, the heat generated at the overlapping portion of the adjacent inspection stripes 20 can be eliminated. Therefore, when acquiring an image, the influence of the heat has been eliminated.

According to the first embodiment, with regard to the inspection of adjacent stripe regions, it is possible to reduce or avoid the influence of inspection of one stripe region to affect the other stripe region. Therefore, high-precision inspection can be performed even for both the adjacent stripe regions.

Second Embodiment

In the first embodiment mentioned above, the inspection stripe 20 is scanned with a laser light. In the second embodiment, the case of inspection with an electron beam will be described.

Figure 8:
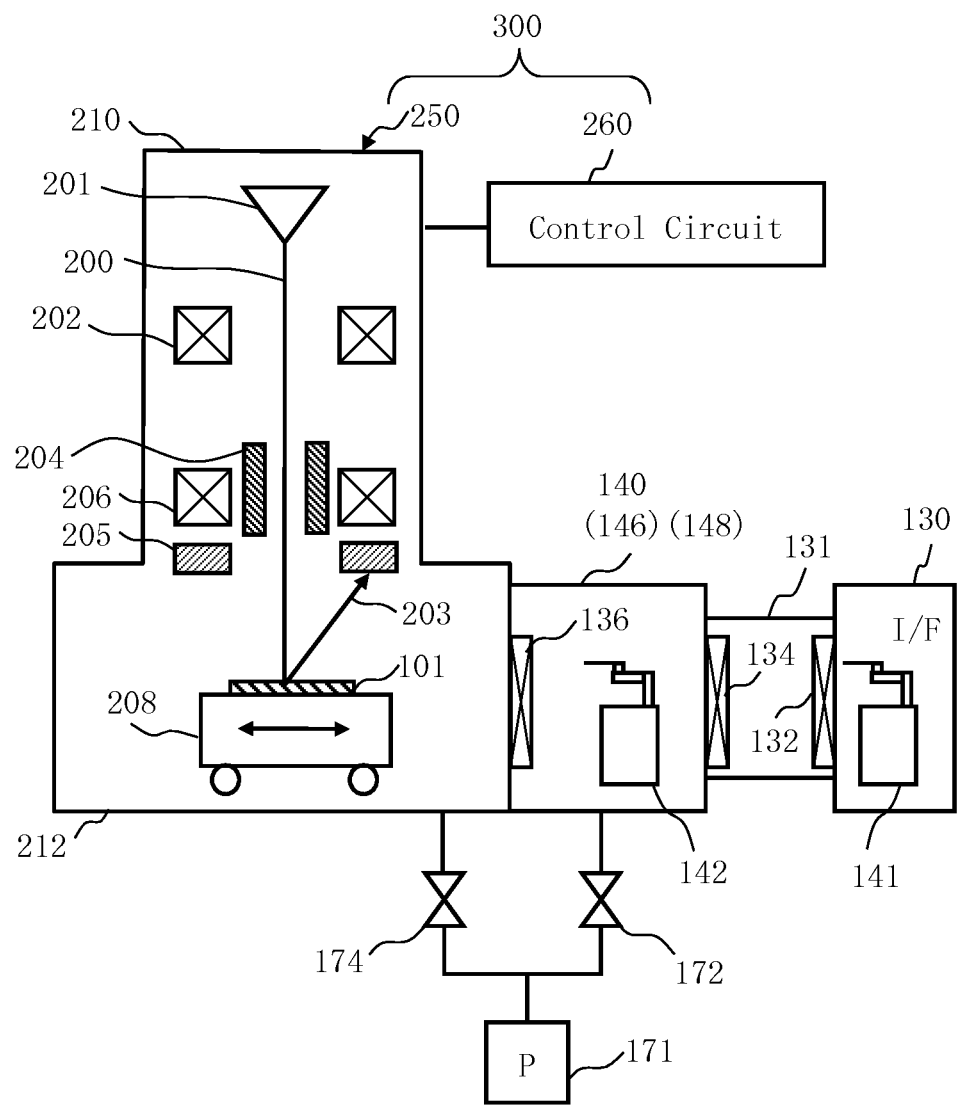
FIG. 8 is a schematic diagram showing a structure of a pattern inspection apparatus according to the second embodiment.

FIG. 8 is a schematic diagram showing a structure of a pattern inspection apparatus according to the second embodiment. In FIG. 8, an inspection apparatus 300 that inspects a defect of a pattern formed on the target object, such as a mask, includes an inspection unit 250, a control system circuit 260 (control unit), the input/output interface (I/F) 130, the load lock chamber 131, the robot chamber 140, the cooling chamber 146, an electric discharge chamber 148, and a vacuum pump 171. The inspection unit 250 includes an electron lens barrel 210 and an inspection chamber 212. In the electron lens barrel 210, there are arranged an electron gun assembly 201, a projection lens 202, a deflector 204, a detector 205, and an objective lens 206. A movable XYθ table 208 is arranged in the inspection chamber 212. The target object 101 is placed on the XYθ table 208. The target object 101 is, for example, an exposure mask substrate used for transferring a pattern onto the wafer. A pattern composed of a plurality of figures to be inspected is formed on this mask substrate.

In the input/output interface 130, the transfer robot 141 for transferring the target object 101 is arranged. In the robot chamber 140, the transfer robot 142 for transferring the target object 101 is arranged. The vacuum pump 171 exhausts the gas in the robot chamber 140 through a valve 172. Thereby, the inside of the robot chamber 140 is maintained to be vacuum atmosphere. Moreover, the vacuum pump 171 exhausts the gas in the inspection chamber 212 through a valve 174. Thereby, the inside of the inspection chamber 212 is maintained to be vacuum atmosphere. In addition, the gate valves 132, 134, and 136 are arranged at the boundaries each between two of the input/output interface 130, the load lock chamber 131, the robot chamber 140, and the inspection chamber 212.

FIG. 8 shows a configuration necessary for describing the second embodiment. It should be understood that other configuration elements generally necessary for the inspection apparatus 300 may also be included therein. The transfer robots 141 and 142 may be any as long as they are mechanical systems, such as an elevator mechanism and a rotation mechanism.

Figure 9:
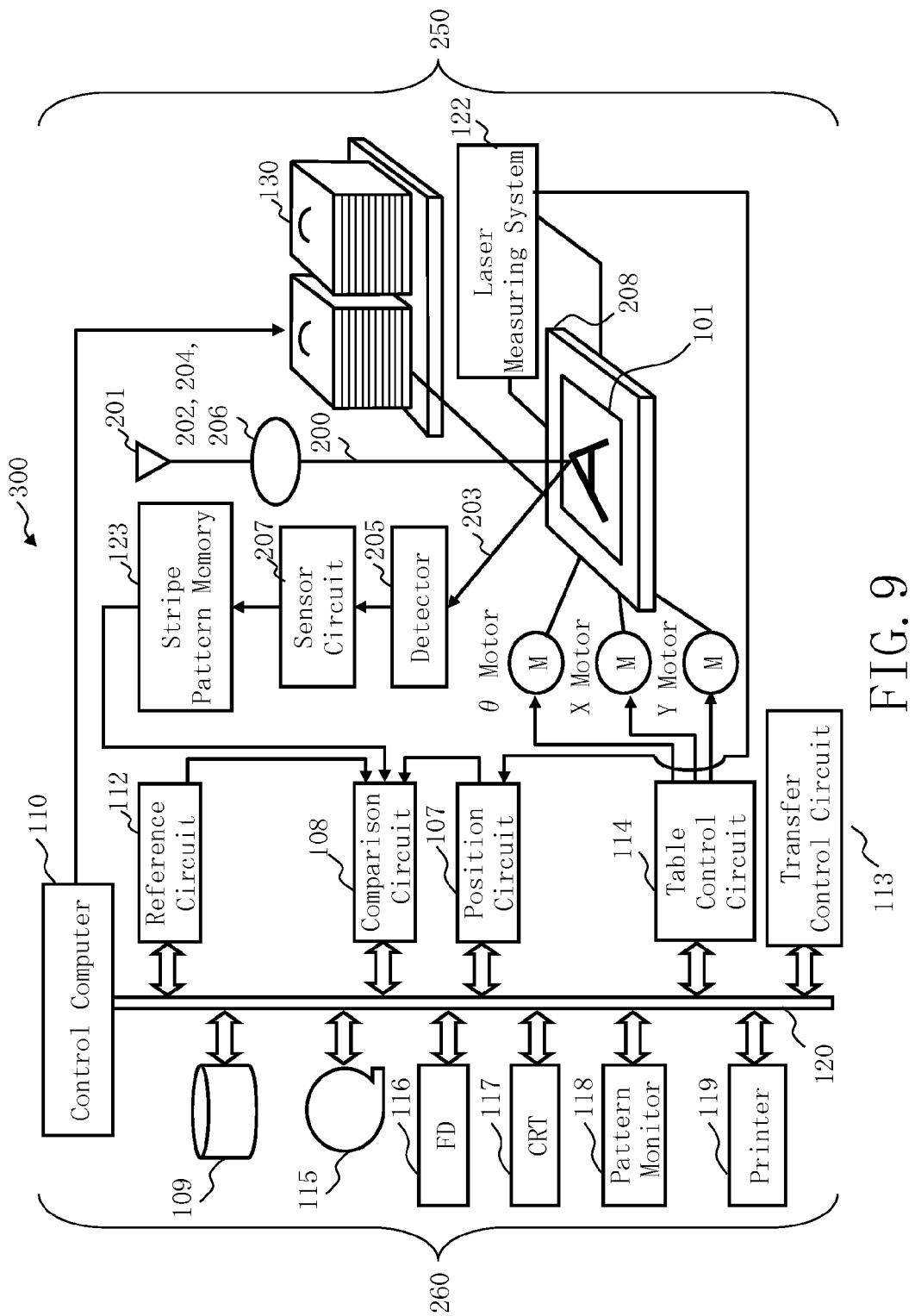
FIG. 9 is a conceptual diagram showing a configuration of an inspection apparatus according to the second embodiment.

FIG. 9 is a conceptual diagram showing a configuration of an inspection apparatus according to the second embodiment. In FIG. 9, the inspection unit 250 further includes a sensor circuit 207, the stripe pattern memory 123, and the laser measuring system 122. In the control system circuit 160, the control computer 110 is connected, through the bus 120, to the position circuit 107, the comparison circuit 108, the reference circuit 112, the transfer control circuit 113, the table control circuit 114, the magnetic disk drive 109, the magnetic tape drive 115, the flexible disk drive (FD) 116, the CRT 117, the pattern monitor 118, and the printer 119. Moreover, the sensor circuit 207 is connected to the stripe pattern memory 123 which is connected to the comparison circuit 108. The XYθ table 208 is driven by an X-axis motor, a Y-axis motor, and a θ-axis motor. The XYθ table 208 serves as an example of the stage.

In the inspection apparatus 300, an inspection optical system of large magnification is composed of the electron gun assembly 201, the projection lens 202, the deflector 204, the detector 205, the objective lens 206, and the sensor circuit 207. The XYθ table 208 is driven by the table control circuit 114 under the control of the control computer 110. The XYθ table 208 can be moved by a drive system such as a three-axis (X, Y, and θ) motor, which drives in the directions of x, y, and θ. For example, a step motor can be used as each of these X, Y, and θ motors. The XYθ table 208 is movable in the horizontal direction and a rotation direction by the X-, Y-, and θ-axis motors. The moving position of the XYθ table 208 is measured by the laser measuring system 122 and supplied to the position circuit 107.

The photo-mask 101 serving as an inspection target object, on which a plurality of figure patterns are formed, is placed on the XYθ table 208 by the transfer operation controlled by the transfer control circuit 113 to be described later. An electron beam 200 emitted from the electron gun assembly 201 is projected by the projection lens 202. The electron beam focused by the objective lens 206 irradiates a desired position on the photomask 101. Then, the detector 205 detects a reflected electron or a secondary electron generated at the inspection region of the photo mask 101 by irradiation of the electron beam 200. It is preferable to use, for example, a line sensor in which a plurality of detection elements are arranged or a two-dimensional sensor, as the detector 205. For example, it is more preferable to use a TDI (Time Delay Integration) sensor, etc. for electron beams. Since pixel data is accumulated by using the TDI sensor, errors can be averaged.

Figure 10:
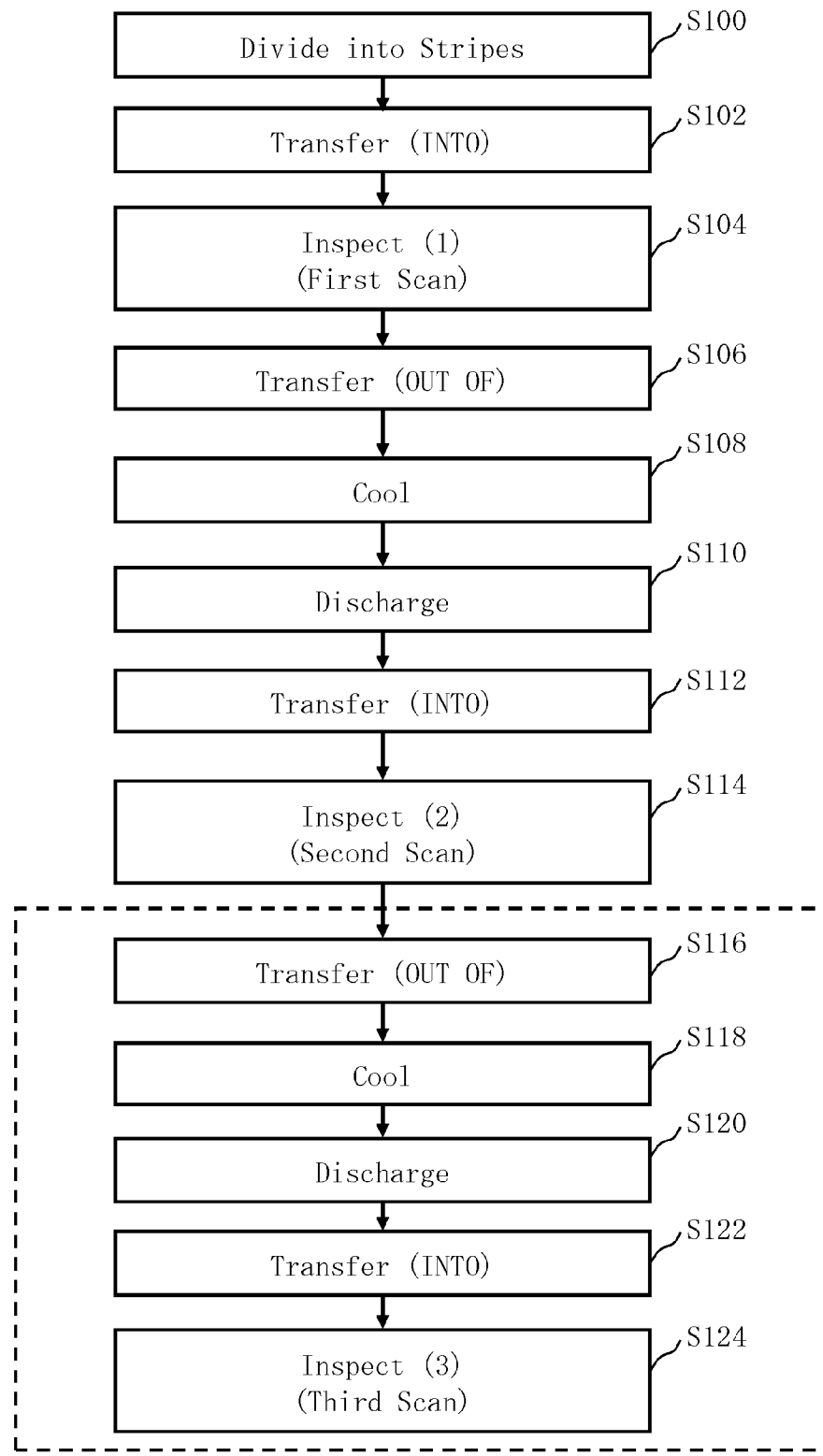
FIG. 10 is a flowchart showing main steps of an inspection method according to the second embodiment.

FIG. 10 is a flowchart showing main steps of an inspection method according to the second embodiment. In FIG. 10, the inspection method according to the second embodiment executes a series of steps: the step (S100) of dividing into stripes, the transferring-in step (S102), the inspection (1) step (S104), the transferring-out step (S106), the cooling step (S108), an electric discharge step (S110), the transferring-in step (S112), and the inspection (2) step (S114). Here, the case where a plurality of inspection stripes 20 are separated into two groups (stripe region groups) is shown. Moreover, if a plurality of inspection stripes 20 are separated into three groups as to be described later, there will be executed a further series of steps: the transferring-out step (S116), the cooling step (S118), an electric discharge step (S120), the transferring-in step (S122), and the inspection (3) step (S124). The contents of the second embodiment are the same as those of the first embodiment except what is particularly described below.

The contents of the step (S100) of dividing into stripes are the same as those of the first embodiment. The width in the short side direction of the inspection stripe 20 may be the same as the size of the electron beam 200, or may be several times the size of the electron beam 200. Thus, it is preferable for the size of the electron beam 200 to be the size which can irradiate the region for a plurality of pixels at a time. However, it is not limited thereto, and may be the size for one pixel.

In the transferring-in step (S102), the target object 101 is transferred into the inspection chamber 212. Similarly to the first embodiment, after the gate valve 132 is opened, the target object 101 arranged in the input/output interface 130 (on the autoloader) is transferred to the stage in the load lock chamber 131 by the transfer robot 141. Then, after the gate valve 132 is closed, the gate valve 134 is opened in order to transfer the target object 101 onto the XYθ table 208 in the inspection chamber 212 through the robot chamber 140 by the transfer robot 142.

Figure 11:
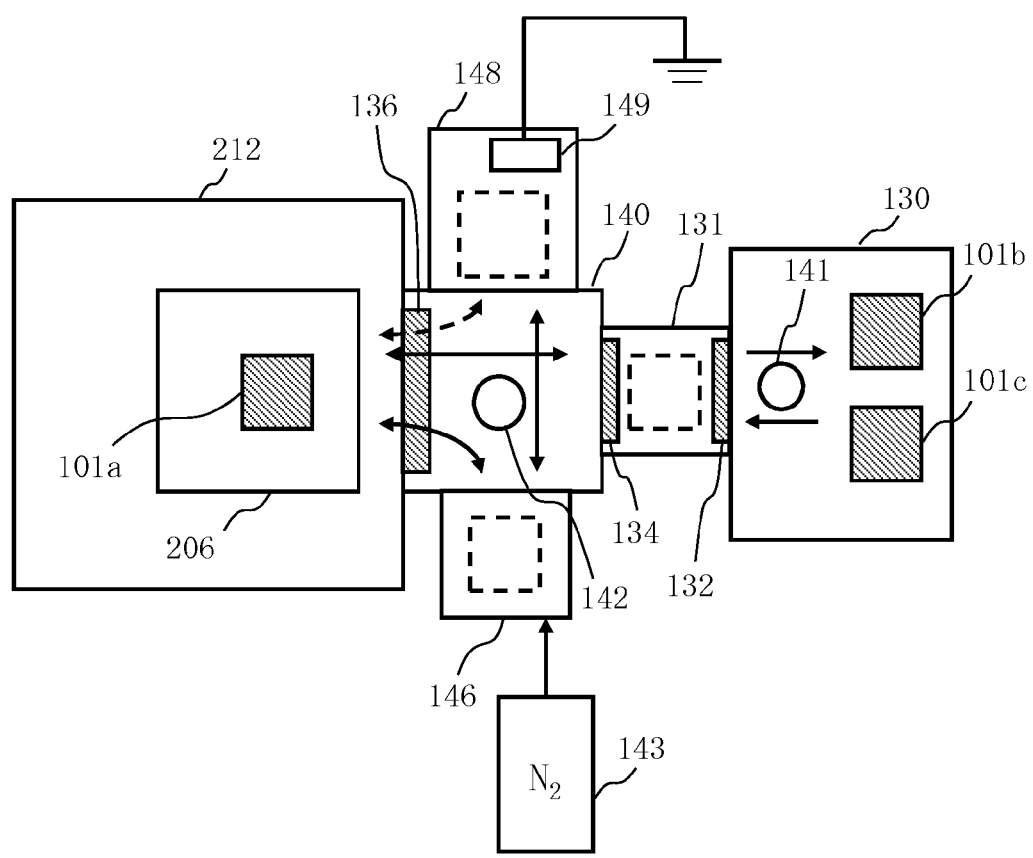
FIG. 11 is a top view schematic diagram showing a transfer route in an inspection apparatus according to the second embodiment.

FIG. 11 is a top view schematic diagram showing a transfer route in an inspection apparatus according to the second embodiment. After the gate valve 132 is opened, the target object 101 arranged in the input/output interface 130 (on the autoloader) is transferred to the stage in the load lock chamber 131 by the transfer robot 141. Then, after the gate valve 132 is closed, the gate valve 134 is opened in order to transfer the target object 101 onto the XYθ table 208 in the inspection chamber 151 through the robot chamber 140 by the transfer robot 142.

In the inspection (1) step (S104), after the target object 101 is placed on the XYθ table 208 and the gate valve 136 is closed, inspection of a pattern formed on the target object 101 on the XYθ table 208 is carried out. Here, inspection (the first scan) (the first image acquisition) is performed with respect to inspection stripes 20 of the first group (the first stripe region group) in a plurality of inspection stripes 20.

As shown in FIG. 6, a set of every other inspection stripes 20 in a plurality of inspection stripes 20 is specified as the first group inspection stripes 20. A set of the remaining every other inspection stripes 20, such as S2, S4, S6, . . . , is specified as the second group inspection stripes 20.

Then, with respect to each of the inspection stripes 20 of the first group, defect inspection is performed for a figure pattern arranged in a stripe region concerned using the electron beam 200 in the longitudinal direction (the x direction) of the stripe region concerned. Here, the movement of the XYθ table 208 is controlled such that the inspection stripes 20 of the first group are scanned continuously. Inspection images are acquired by the detector 205 while the irradiation position of the electron beam 200 moves relatively in the x direction continuously by the movement of the XYθ table 208. The detector 205 continuously captures optical images each having a scan width W as shown in FIG. 4. In other words, the detector 205, being an example of a sensor, captures optical images of a plurality of figure patterns formed on the photo-mask 101 by using an electron beam, while moving relatively to the XYθ table 208 (stage). According to the second embodiment, after capturing an optical image in one inspection stripe 20 (for example, S1), the detector 205 moves in the y direction to the position of the next inspection stripe 20 (for example, S3) of the same group and similarly captures another optical image having the scan width W continuously while moving in the direction reverse to the last image capturing direction. That is, the image capturing is repeated in the forward (FWD) to backward(BWD) direction, namely going in the reverse direction when advancing and returning.

The direction of the image capturing is not limited to repeating the forward(FWD) and backward(BWD) movement. It is also acceptable to capture an image from a fixed one direction with respect to each inspection stripe 20 of the same group. For example, repeating FWD and FWD may be sufficient, and alternatively, BWD and BWD may also be sufficient.

In the case of the size of the electron beam 200 being smaller than the width in the short side direction of the inspection stripe 20, the deflector 204 performs scanning with an electron beam in the direction of the short side of the inspection stripe 20 while the XYθ table 208 is being moved. Thereby, data for all the pixels in the direction of the short side of the inspection stripe 20 can be detected.

The image of the pattern detected by the detector 205 is amplified by each detection element of the detector 205, and is further analog-to-digital (A/D) converted by the sensor circuit 206. Then, pixel data for each inspection stripe is stored in the stripe pattern memory 123. The pixel data is sent to the comparison circuit 108, with data indicating the position of the photo-mask 101 on the XYθ table 208 output from the position circuit 107. Measurement data is 8-bit unsigned data, for example, and indicates a gray level (light intensity) of brightness of each pixel.

In the comparison step, each pixel data of measurement data and reference pixel data of reference data are compared with each other for each pixel by the comparison circuit 108 (comparison unit) in accordance with a predetermined algorithm in order to determine the existence or nonexistence of a defect.

As described above, first, pattern defect inspection is performed with respect to inspection stripes 20 of the first group. Through the above inspection (1) step (S104), the inspection stripes 20 of the first group have been heated by an electron beam. Further, charging up occurs due to the electron beam. Therefore, in this state, if scanning is performed for an inspection stripe 20 adjacent to each of the inspection stripes 20 of the first group, an image acquired at the adjacent inspection stripe 20 may be distorted. Therefore, the target object 101 is once cooled and discharged before carrying out the inspection (2) step (S114).

In the transferring-out step (S106), when a pattern defect inspection has been completed with respect to all the inspection stripes 20 of the first group, the target object 101 is moved (transferred) into the robot chamber 140 from the XYθ table 208 in the inspection chamber 212 by the transfer robot 142. Then, after the gate valve 136 is closed, the target object 101 is transferred to the stage in the cooling chamber 146.

In the cooling step (S108), the target object 101 is cooled in the cooling chamber 146 (an example of the cooling unit). The heat resulting from scanning the inspection stripes 20 of the first group can be eliminated by cooling the target object 101. After cooling, the target object 101 is moved (transferred) into the robot chamber 140 from the cooling chamber 146 by the transfer robot 142. Then, the target object 101 is transferred onto the stage in the electric discharge chamber 148.

In the electric discharge step (S110), electric potential charged up in the inspection region of the target object 101 is discharged in the electric discharge chamber 148 (an example of an electric discharge unit). The negative electric potential resulting from scanning the inspection stripes 20 of the first group can be eliminated by performing discharge of the target object 101. An ionizer 149 (an electric discharge unit or a neutralization unit) is arranged as an electric discharge mechanism in the electric discharge chamber 148. The electric potential charged in the inspection stripe 20 is electrically neutralized or discharged by the ionizer 149.

In the transferring-in step (S112), after the target object 101 has been cooled and discharged, the target object 101 is moved (transferred) into the robot chamber 140 from the stage in the electric discharge chamber 148 by the transfer robot 142. Then, the gate valve 136 is opened in order to transfer the target object 101 onto the XYθ table 208 in the inspection chamber 212. The pressure increase in the cooling chamber 146 or robot chamber 140 by the coolant gas may be adjusted by exhausting the gas by the vacuum pump 171.

In the inspection (2) step (S114), after the target object 101 is placed on the XYθ table 208 and the gate valve 136 is closed, inspection (2) of a pattern formed on the target object 101 on the XYθ table 208 is carried out. Here, inspection (the second scan) (the second image acquisition) is performed with respect to inspection stripes 20 of the second group (the second stripe region group) in a plurality of inspection stripes 20.

Then, with respect to each of the inspection stripes 20, such as S2, S4, S6, . . . , of the second group, defect inspection is performed for a figure pattern arranged in a stripe region concerned using an electron beam, in the longitudinal direction (the x direction) of the stripe region concerned. Here, the movement of the XYθ table 208 is controlled such that the inspection stripes 20 of the second group are scanned continuously. The inspection method is the same as that for inspection stripes 20 of the first group.

As described above, in the example of FIG. 6, each of every other inspection stripes 20 in a plurality of inspection stripes 20 obtained by dividing the entire inspection region of the target object 101 is scanned with an electron beam as the first scan. After the first scanning, cooling and discharging (electric neutralizing) is performed. Then, each of the remaining every other inspection stripes 20 is scanned with an electronic beam as the second scan. Thereby, the influence of the heat and charged potential resulting from scanning the adjacent inspection stripe 20 can be eliminated. Therefore, the influence of the heat and charged potential generated by the first scan has been eliminated when performing the second image acquisition.

Moreover, it goes without saying that it is also preferable to group every three inspection stripes as shown in FIG. 7. The first group inspection stripes 20 are configured by inspection stripes 20, such as S1, S4, S7, . . . , which are every three inspection stripes and each of which does not include the adjacent stripe region. The second group inspection stripes 20 are configured by inspection stripes 20, such as S2, S5, S8, . . . , which are every three inspection stripes and each of which does not include the adjacent stripe region. The third group inspection stripes 20 are configured by inspection stripes 20, such as S3, S6, S9, . . . , which are every three inspection stripes and each of which does not include the adjacent stripe region.

After performing each step from the step (S100) of dividing into stripes to the inspection (2) step (S114) described above, further the transferring-out step (S116), the cooling step (S118), the discharge step (S120), the transferring-in step (S122), and the inspection (3) step (S124) are carried out. The inspection (1) step (S104) is executed not for S1, S3, S5, . . . , which are every other inspection stripes 20 but for S1, S4, S7, . . . , which are every three inspection stripes 20. Similarly, the inspection (2) step (S114) is executed not for S2, S4, S6, . . . , which are every other inspection stripes 20 but for S2, S5, S8, . . . , which are every three inspection stripes 20.

In the transferring-out step (S116), when a pattern defect inspection has been completed with respect to all the inspection stripes 20 of the second group, the gate valve 136 is opened in order to move (transfer) the target object 101 into the robot chamber 140 from the XYθ table 208 in the inspection chamber 212 by the transfer robot 142. Then, after the gate valve 136 is closed, the target object 101 is transferred onto the stage in the cooling chamber 146.

In the cooling step (S118), the target object 101 is cooled in the cooling chamber 146. The cooling method is the same as that of the cooling step (S108).

In the electric discharge step (S120), electric potential charged up in the inspection region of the target object 101 is discharged in the electric discharge chamber 148 (an example of the electric discharge unit). The electric discharge method is the same as that of the electric discharge step (S110).

In the transferring-in step (S122), after the target object 101 has been cooled, the target object 101 is moved (transferred) into the robot chamber 140 from the stage in the discharge chamber 148 by the transfer robot 142. Then, the gate valve 136 is opened in order to transfer the target object 101 to the XYθ table 208 in the inspection chamber 212. The pressure increase in the cooling chamber 146 or robot chamber 140 by the coolant gas may be adjusted by exhausting the gas by the vacuum pump 171.

In the inspection (3) step (S124), after the target object 101 is placed on the XYθ table 208 and the gate valve 136 is closed, inspection (3) of a pattern formed on the target object 101 on the XYθ table 208 is carried out. Here, inspection (the third scan) (the third image acquisition) is performed with respect to inspection stripes 20 of the third group (the third stripe region group) in a plurality of inspection stripes 20.

Then, with respect to each of the inspection stripes 20, such as S3, S6, S9, . . . , of the third group, defect inspection is performed for a figure pattern arranged in a stripe region concerned using an electron beam, in the longitudinal direction (the x direction) of the stripe region concerned. Here, the movement of the XYθ table 208 is controlled such that the inspection stripes 20 of the third group are scanned continuously. The inspection method is the same as that for the inspection stripes 20 of the second group.

As described above, according to the second embodiment, the influence of the heat and charged potential resulting from scanning the adjacent inspection stripe 20 can be eliminated. Therefore, the influence of the heat and charged potential generated by the first scan has been eliminated when performing the second image acquisition. The influence of the heat and charged potential generated by the second scan (and the first scan) has been eliminated when performing the third image acquisition.

Then, after the inspection of all the inspection stripes has been completed, the gate valve 136 is opened in order to transfer the target object 101 into the robot chamber 140 from the XYθ table 208 in the inspection chamber 212 by the transfer robot 142. After the gate valve 136 is closed, the gate valve 134 is opened in order to transfer the target object 101 onto the stage in the load lock chamber 131 by the transfer robot 142. Then, after the gate valve 134 is closed, the gate valve 132 is opened in order to transfer the target object 101 to the input/output interface 130 by the transfer robot 141.

As described above, according to the second embodiment, inspection stripes 20 adjacent to each other are separated into different groups in order to perform scanning per group with an electron beam, and the target object is cooled between the scanning of each group. Thereby, the influence of the heat and charged potential resulting from scanning the adjacent inspection stripe 20 can be eliminated. Therefore, when acquiring an image, the influence of the heat and charged potential has been eliminated.

According to the second embodiment, as well as the first embodiment, with regard to the inspection of adjacent stripe regions, it is possible to reduce or avoid the influence of inspection of one stripe region to affect the other stripe region. Particularly, the heat and charged potential generated at the overlapping portion of the adjacent inspection stripes 20 can be eliminated. Therefore, high-precision inspection can be performed even for both the adjacent stripe regions.

What is described as a "circuit" or "step" in the above description can be configured by hardware such as an electronic circuit etc. or by a computer operable program. Alternatively, they may be implemented not only by a program being software but by a combination of hardware and software, or further, by a combination of hardware, software and firmware. When configured by a program, the program is stored in a computer readable recording medium, such as a magnetic disk drive, a magnetic tape drive, FD, or ROM (Read Only Memory). For example, the table control circuit 114, the reference circuit 112, the comparison circuit 108, etc. which constitute the operation control unit may be configured by an electric circuit. Alternatively, they may be implemented as software to be processed by the control computer 110, or implemented by a combination of electric circuits and software.

Referring to specific examples, embodiments have been described above. However, the present invention is not limited to these examples. For example, the transmission illumination optical system which uses a transmitted light is described as an illumination optical system 170 in the embodiments, but it is not limited thereto. For example, it may be a reflection illumination optical system which uses a reflected light. Alternatively, it is also acceptable to simultaneously use a transmitted light and a reflected light by combining the transmission illumination optical system and the reflection illumination optical system. Moreover, although a die-to-database inspection that compares measurement data with a reference image generated from design data is performed in the embodiments, it is not limited thereto. It is also preferable to perform a die-to-die inspection that compares measurement data with each other by using a photo mask where identical patterns are formed.

Although, in the second embodiment, both cooling and electric discharging are carried out, it is also acceptable to perform either one of them. The accuracy of the effect may be lower than that of the case of performing the both, but however, effect to some extent can be obtained even when performing only one of them.

Although, in the examples described above, inspection stripes are regularly grouped, such as a group of every other inspection stripes or a group of every three inspection stripes, it is not limited thereto. It is also acceptable to group inspection stripes irregularly as long as inspection stripes adjacent to each other are not included in the same group. Moreover, the number of groups may be four or more. Cooling and/or electric discharging should be performed between inspections of each group.

While the apparatus configuration, control method, and the like not directly necessary for explaining the present invention are not described, some or all of them may be suitably selected and used when needed. For example, although description of the configuration of a control unit for controlling the inspection apparatus 100 is omitted, it should be understood that some or all of the configuration of the control unit is to be selected and used appropriately when necessary.

In addition, any other pattern inspection apparatus and pattern inspection method that include elements of the present invention and that can be appropriately modified by those skilled in the art are included within the scope of the present invention.

Additional advantages and modification will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A pattern inspection method comprising:
   acquiring an image of a figure pattern arranged in each of stripe regions of a first group of stripe regions not including adjacent stripe regions in a plurality of stripe regions obtained by virtually dividing an inspection region of a target object on which a plurality of figure patterns have been formed into the plurality of stripe regions each having a strip shape and overlapping a part of an adjacent stripe region, wherein the acquiring is performed using one of a laser light and an electron beam, in a longitudinal direction of the stripe region of the first group such that the stripe regions of the first group not including adjacent stripe regions are scanned continuously; and
   acquiring, after the acquiring the image of the figure pattern has been completed for all of the stripe regions of the first group, an image of a figure pattern arranged in each of stripe regions of a second group of stripe regions not including adjacent stripe regions, in remaining stripe regions other than the stripe regions of the first group in the plurality of stripe regions, wherein the acquiring is performed using one of the laser light and the electron beam, in the longitudinal direction of the stripe region of the second group such that the stripe regions of the second group not including adjacent stripe regions are scanned continuously.

2. The method according to claim 1, further comprising:
   cooling the target object after the acquiring the image of the figure pattern has been completed for all of the stripe regions of the first group.

3. The method according to claim 2, further comprising:
   acquiring, after the acquiring the image of the figure pattern has been completed for all of the stripe regions of the second group, an image of a figure pattern arranged in each of stripe regions of a third group of stripe regions not including adjacent stripe regions, in remaining stripe regions other than the stripe regions of the first group and the second group in the plurality of stripe regions, wherein the acquiring is performed using one of the laser light and the electron beam, in the longitudinal direction of the stripe region of the third group.

4. The method according to claim 1, wherein, after inspecting a defect of the figure pattern has been completed for all of the stripe regions of the first group in an inspection chamber, the target object is transferred out of the inspection chamber, and transferred into the inspection chamber before inspecting a defect of the figure pattern of each of the stripe regions of the second group.

5. The method according to claim 1, further comprising:
reading design data in order with respect to each of the stripe regions of the first group; and
converting the design data having been read into image data in order to generate a reference image.

6. The method according to claim 5, wherein the image of each of the stripe regions of the first group is divided into a plurality of frame images of a predetermined size.

7. The method according to claim 6, further comprising:
comparing each frame image of the plurality of frame images with a corresponding reference image, for each pixel, in accordance with a predetermined algorithm.

8. The method according to claim 1, wherein the image of the figure pattern has been acquired with respect to all of the stripe regions of the first group in an inspection chamber, further comprising:
transferring the target object out of the inspection chamber after the acquiring the image of the figure pattern has been completed for all of the stripe regions of the first group.

9. The method according to claim 8, further comprising:
cooling the target object outside the inspection chamber, after the transferring the target object out of the inspection chamber.

10. The method according to claim 8, further comprising:
discharging electric potential, which has been charged up in the target object, outside the inspection chamber, after the transferring the target object out of the inspection chamber.

11. A pattern inspection method comprising:
inspecting a defect of a figure pattern arranged in each of stripe regions of a first group of stripe regions not including adjacent stripe regions in a plurality of stripe regions obtained by virtually dividing an inspection region of a target object on which a plurality of figure patterns are formed into the plurality of stripe regions each having a strip shape and overlapping a part of an adjacent stripe region, wherein the inspecting is performed using one of a laser light and an electron beam, in a longitudinal direction of the stripe region of the first group such that the stripe regions of the first group not including adjacent stripe regions are scanned continuously;
cooling the target object after the inspecting the defect of the figure pattern has been completed for all of the stripe regions of the first group; and
inspecting, after the cooling, a defect of a figure pattern arranged in each of stripe regions of a second group of stripe regions not including adjacent stripe regions, in remaining stripe regions other than the stripe regions of the first group in the plurality of stripe regions, wherein the inspecting is performed using one of the laser light and the electron beam, in the longitudinal direction of the stripe region of the second group such that the stripe regions of the second group not including adjacent stripe regions are scanned continuously.

12. A pattern inspection apparatus comprising:
an inspection chamber where inspection of a defect of a figure pattern of a target object on which a plurality of figure patterns are formed is performed using one of a laser light and an electron beam; and
a cooling unit arranged outside the inspection chamber and configured to cool the target object after the target object is transferred into the cooling unit.

13. A pattern inspection apparatus comprising:
an inspection chamber where inspection of a defect of a figure pattern of a target object on which a plurality of figure patterns are formed is performed using one of a laser light and an electron beam; and
an electric discharge unit arranged outside the inspection chamber and configured to discharge electric potential which has been charged up in the target object, from the target object, after the target object is transferred into the electric discharge unit.

* * * * *